(12) United States Patent
De Jong et al.

(10) Patent No.: US 7,017,209 B1
(45) Date of Patent: Mar. 28, 2006

(54) CURVED WING BOARD FOR A CT CRADLE

(75) Inventors: Travis S. De Jong, Orange City, IA (US); Thomas G. Kockler, Remsen, IA (US)

(73) Assignee: Medtec, Inc., Orange City, IA (US)

( * ) Notice: Subject to any disclaimer, the term of this patent is extended or adjusted under 35 U.S.C. 154(b) by 0 days.

(21) Appl. No.: 11/079,807

(22) Filed: Mar. 14, 2005

(51) Int. Cl.
*A61B 6/00* (2006.01)
*A61G 7/07* (2006.01)

(52) U.S. Cl. ............... 5/601; 5/621; 5/632; 378/20; 378/208

(58) Field of Classification Search ............ 5/621–623, 5/601, 632, 640, 643, 646; 378/20, 208, 378/209
See application file for complete search history.

(56) References Cited

U.S. PATENT DOCUMENTS

| | | | |
|---|---|---|---|
| 1,375,235 A | 4/1921 | Richards | |
| 3,966,200 A | 6/1976 | Kirk | |
| 4,034,224 A | 7/1977 | Heavens et al. | |
| 4,198,044 A | 4/1980 | Holappa | |
| 4,475,072 A | 10/1984 | Schwehr et al. | |
| 4,484,571 A * | 11/1984 | Velazquez | 5/601 |
| 4,681,308 A | 7/1987 | Rice | |
| 4,688,780 A * | 8/1987 | Hanz | 5/621 |
| 4,915,101 A | 4/1990 | Cuccia | |
| 5,195,938 A * | 3/1993 | Robertson | 482/131 |
| 5,337,427 A * | 8/1994 | Pagano et al. | 5/602 |
| 5,433,220 A | 7/1995 | Kostich | |
| 5,467,782 A | 11/1995 | Wiseman | |
| 5,537,702 A * | 7/1996 | Brown-Milants et al. | 5/632 |
| 5,619,763 A | 4/1997 | Randolph et al. | |
| 5,623,949 A | 4/1997 | Kostich | |
| 5,724,992 A * | 3/1998 | Ip | 128/845 |
| 6,452,999 B1 | 9/2002 | Maida | |

* cited by examiner

*Primary Examiner*—Robert G. Santos
(74) *Attorney, Agent, or Firm*—McKee, Voorhees & Sease, P.L.C.

(57) ABSTRACT

A curved wing board is provided for use on a CT cradle having a curved upper surface. The wing board includes a base with a curved lower surface and opposite sides. A pair of wing boards extend upwardly and outwardly from the sides of the base to support a patient's arms raised above their head. A pair of hand grips are provided on the base for gripping by the patient. The curved wing board matingly engages the curved CT cradle so as to comfortably support the patient in a stable orientation during CT imaging.

21 Claims, 4 Drawing Sheets

CURVED WING BOARD FOR A CT CRADLE

BACKGROUND OF THE INVENTION

CT imaging is commonly used for two purposes. First, diagnostic imaging wherein a patient is positioned within a bore of a CT imaging machine allows physicians and other medical personnel to view internal slices of a patient's body, though generally not for cancer detection. Second, CT imaging is used for radiation therapy planning for treatment of cancerous tumors through the use of a linear accelerator. In both procedures, a CT cradle is used for positioning the patient. However, in the diagnostic imaging, the cradle has a curved upper surface, whereas in the radiation therapy process, the medical technician must use a flat surface or tabletop mounted to the curved CT cradle to accommodate the flat surface of the linear accelerator, which does not have an open bore as in the CT machine. Thus, the two processes require different patient support equipment. The present invention is directed towards the first use of CT imaging wherein a patient is positioned within the relatively small circular bore of the CT machine.

A primary objective of the present invention is the provision of a curved wing board for use with the curved CT cradle for positioning the patient during CT imaging.

Another objective of the present invention is the provision of a curved wing board which matingly engages the curved CT cradle while allowing the patient's arms to be positioned comfortably above their head.

A further objective of the present invention is the provision of a curved wing board which facilitates CT imaging of a patient's torso without interference from the patient's arms.

Still another objective of the present invention is the provision of a curved wing board which safely and securely mounts to a curved CT cradle for use in patient imaging.

Another objective of the present invention is the provision of a curved wing board which is economical to manufacture and durable in use.

These and other objectives will become apparent from the following description of the invention.

SUMMARY OF THE INVENTION

The curved wing board of the present invention is adapted for use with a curved CT cradle. The wing board includes a base having a curved lower surface which matingly engages the curved upper surface of the CT cradle. A pair of wings extends upwardly and outwardly from the base to support a patient's arms in a spaced relation above the cradle. A pair of hand grips are provided at the upper end of the base for gripping by the patient's hands when their arms are extended above their head. One or more fasteners are provided on the base to secure the wing board to the cradle. Preferably, the wing board is symmetrical about a longitudinal center line.

The present invention also is directed towards a method of positioning a patient for a CT scan. The positioning method includes the steps of securing a curved wing board to a curved CT cradle, lying the patient on the board, extending the patient's arms above their head, and supporting the patient's arms with the wings of the board. The positioning method further includes the step of gripping a hand grip on the wing board above the patient's head.

DETAILED DESCRIPTION OF THE PREFERRED EMBODIMENT

The present invention is directed towards a curved wing board 10 adapted for use with a CT cradle 12. The cradle 12 includes a curved upper surface 14. Curved CT cradles are well-known in the art, such as those shown in U.S. Pat. No. 4,475,072 (element 11) and U.S. Pat. No. 6,452,999.

Figure 4:
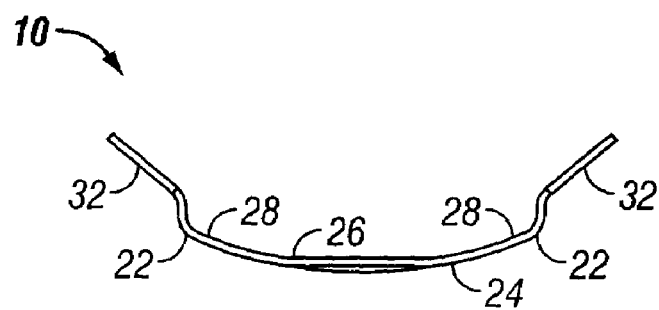
FIG. 4 is an end elevation view of the wing board shown in FIG. 3.
Figure 5:
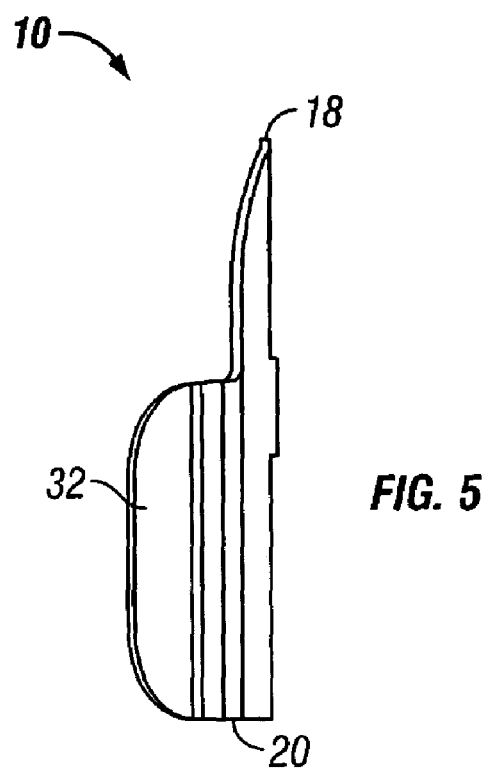
FIG. 5 is a side elevation view of the wing board shown in FIG. 3.
Figure 6:
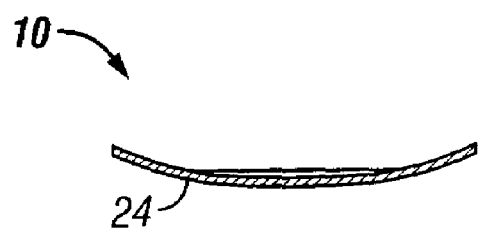
FIG. 6 is a sectional view taken along lines 6—6 of FIG. 3.

The wing board 10 includes a base 16 having a top end 18, a bottom end 20, and opposite sides 22. At least a portion of the base 16 includes a curved lower surface 24, which substantially matches the curved upper surface 14 of the cradle 12, such that the wing board 10 will be stable when positioned on the cradle 12. As seen in FIG. 4, at the bottom end 20 of the base 16, the curvature of the lower surface 24 is defined by a central portion 26 and opposite side portions 28. At a mid-point of the base 16, the bottom surface 24 has a continuous radius, as seen in FIG. 6, matching the curvature of the cradle 12. At both the top end 18 and the bottom end 20 of the base 16, the curvature of the lower surface 24 provides a substantial area of engagement with the upper surface 14 of the cradle 12, such that the wing board 10 stably sits upon the cradle 12.

Figure 1:
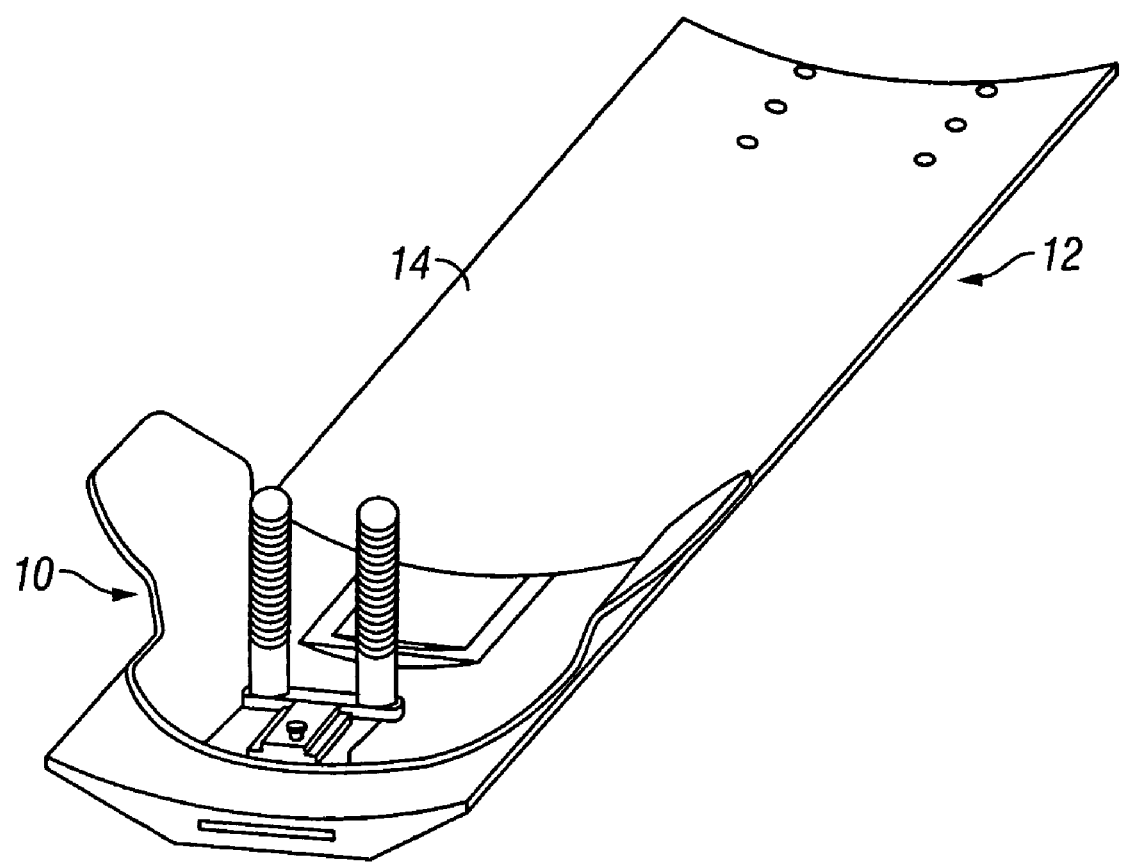
FIG. 1 is a perspective view of a curved CT cradle having the curved wing board of the present invention mounted thereto.
Figure 2:
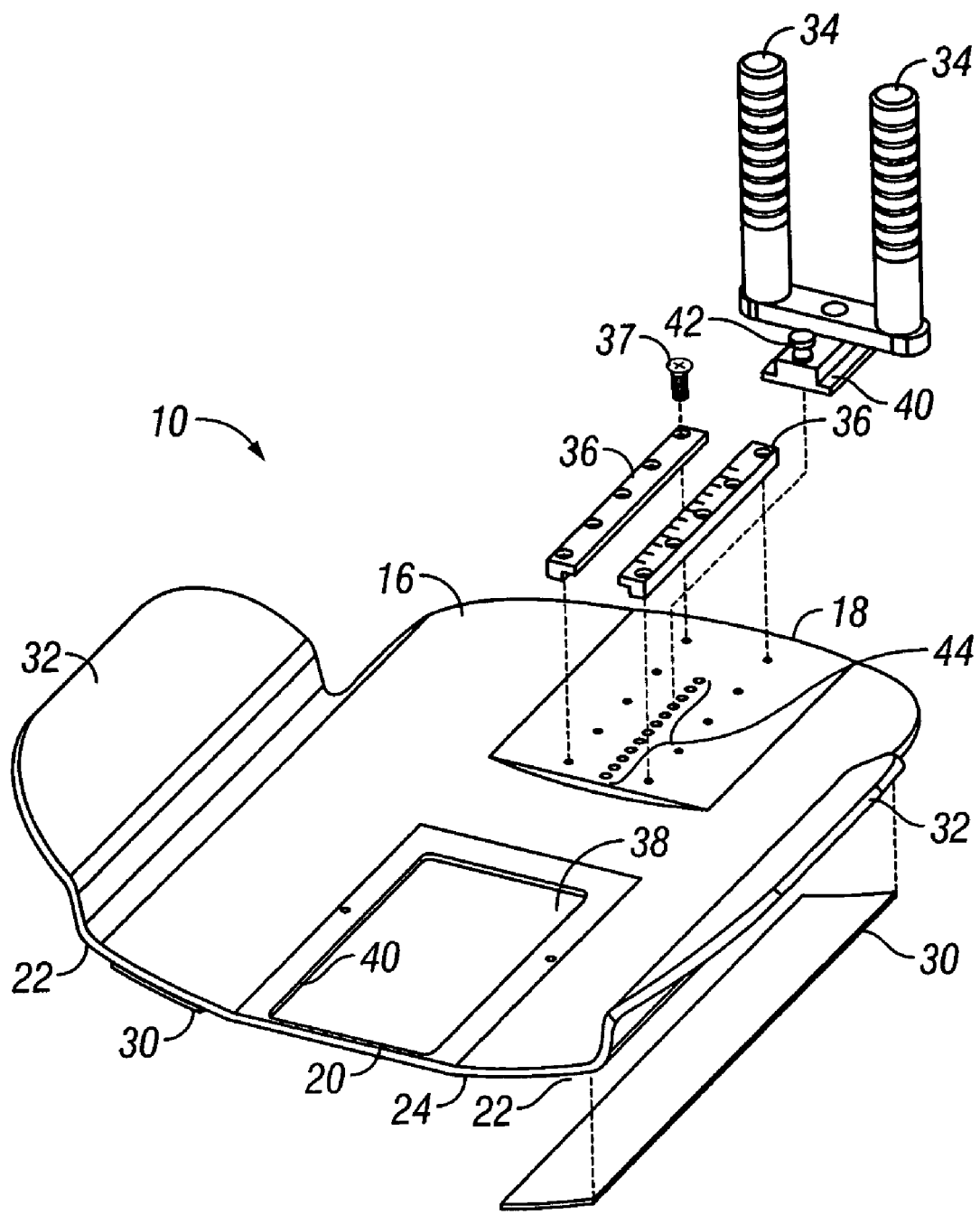
FIG. 2 is an exploded perspective view of the curved wing board of the present invention.
Figure 3:
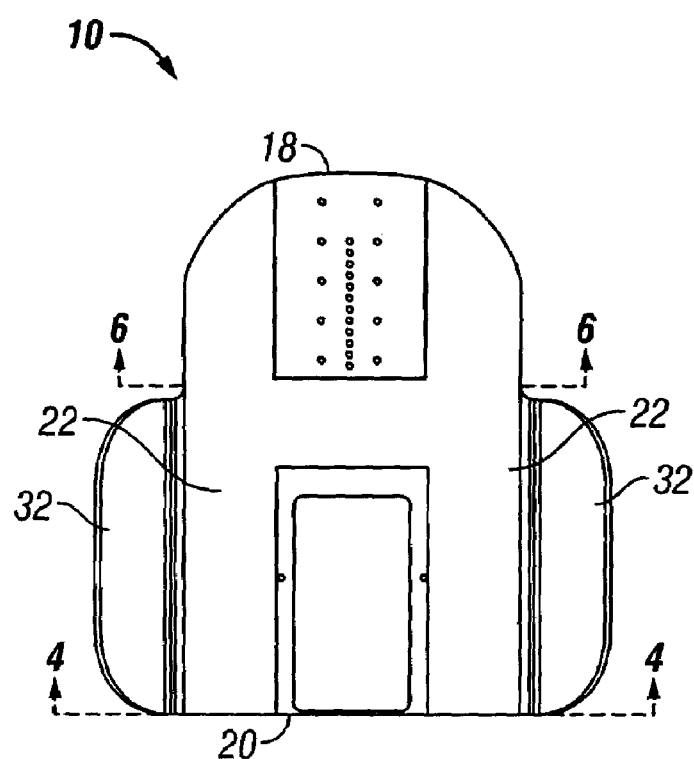
FIG. 3 is a top plan view of the wing board, with the hand grips removed therefrom for clarity.

Fasteners may be provided on the wing board 10 to secure the board to the cradle 12. Fasteners may be any convenient structure. In FIG. 2, the fastener is shown to be Velcro hook or loop strips 30 extending along opposite sides of the lower surface 24 of the base 16, and adapted to engage the corresponding velcro loop or hook (not shown) on the cradle 12.

A pair of wings 32 extend upwardly and outwardly from the opposite sides 22 of the base 16. A pair of hand grips 34 are adjustably mounted on the base 16. More particularly, guide tracks 36 are secured to the base 16 using screws or bolts 37. A foot 40 on the hand grips 34 is slidably received between the tracks 36. A pin 42 extends through the foot 40 for selective receipt in one of a plurality of holes 44 extending along the longitudinal center line of the wing board 10. Thus, the handgrips 34 can be selectively positioned along the tracks 36, depending upon the length of a patient's arms.

The board 10 may also include an area 38 for receiving a head rest (not shown). Preferably the area 38 is recessed so as to define a shoulder or lip 40 for retaining the head rest in position on the board 10.

When the wing board 10 is used for non-cancerous diagnostic CT imaging, the board 10 is secured to the cradle 12 with the hook and loop material 30, or other fasteners, so as to stably sit in a fixed position. The patient is then laid onto the wing board 10 and cradle 12. Next, the patient raises his or her arms above their head, and grips the hand grips 34 while their arms are supported by the wings 32 in a position spaced or raised from the upper surface 14 of the cradle 12. Thus, the patient's upper torso can be imaged using a CT machine, without interference from the patient's arms. The curvature of the wing board 10, the wings 32, and the hand grips 34 provide a comfortable bed or support table for the patient during the CT imaging process.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A curved wing board for use on a CT cradle having a curved upper surface, comprising:
   a base having a curved lower surface and opposite sides;
   a pair of wings rigidly extending upwardly and laterally outwardly from the sides of the base to support a patient's arms raised above their head; and
   a fastener on the base to secure the base to the CT cradle.

2. The curved wing board of claim 1 wherein the curvature of the lower surface of the base corresponds to the curvature of the CT cradle upper surface.

3. The curved wing board of claim 1 wherein the base has a upper end and further comprising a pair of hand grips on the upper end of the wing board.

4. The curved wing board of claim 1 wherein the lower surface of the base has a fixed radius of curvature.

5. The curved wing board of claim 1 wherein the lower surface of the base has a continuous radius of curvature.

6. The curved wing board of claim 1 wherein the wing board is symmetrical about a longitudinal center line.

7. The curved wing board of claim 1 wherein the fastener includes ½ of a hook and loop fastener.

8. The curved wing board of claim 1 wherein the base has top and bottom ends, and the wings extend partially between the top and bottom ends.

9. A curved wing board adapted for use with a curved CT cradle, comprising:
   a base having a curved lower surface to matingly engage the curved CT cradle;
   a pair of rigid wings extending upwardly and laterally outwardly from the base to support a patient's arm in a spaced relation above the cradle;
   a hand grip on the base for gripping by the patient's hands; and
   a fastener on the base to secure the base to the cradle.

10. The curved wing board of claim 9 wherein the lower surface of the base has a fixed radius of curvature.

11. The curved wing board of claim 9 wherein the lower surface of the base has a continuous radius of curvature.

12. The curved wing board of claim 9 wherein the wing board is symmetrical about a longitudinal center line.

13. The curved wing board of claim 9 wherein the fastener includes ½ of a hook and loop fastener.

14. The curved wing board of claim 9 wherein the base has top and bottom ends, and the wings extend partially between the top and bottom ends.

15. A method of positioning a patient for a CT scan, comprising:
   securing a curved board to a curved CT cradle;
   lying the patient on the board;
   extending the patient's arms above their head;
   supporting the patient's arms with wings rigidly extending upwardly and laterally outwardly from opposite sides of the board.

16. The method of claim 15 further comprising gripping a handgrip on the board above the patient's head.

17. The method of claim 15 wherein the arms are spaced from the cradle.

18. The method of claim 15 further comprising matingly engaging the curved wing board to the curved CT cradle.

19. A curved wing board for use on a CT cradle having a curved upper surface, comprising:
   a base having a curved lower surface and opposite sides;
   a pair of wings rigidly extending upwardly and laterally outwardly from the sides of the base to support a patient's arms raised above their head; and
   the curvature of the lower surface of the base corresponding to the curvature of the CT cradle upper surface.

20. The curved wing board of claim 19 wherein the base has a upper end and further comprising a pair of hand grips on the upper end of the wing board.

21. A curved wing board for use on a CT cradle having a curved upper surface, comprising:
   a base having a curved lower surface, an upper end, and opposite sides;
   a pair of wings rigidly extending upwardly and laterally outwardly from the sides of the base to support a patient's arms raised above their head; and
   a pair of hand grips on the upper end of the wing board.

* * * * *